(12) United States Patent
Mazer et al.

(10) Patent No.: US 6,251,432 B1
(45) Date of Patent: Jun. 26, 2001

(54) SUSTAINED RELEASE DOSAGE FORM UNIT HAVING LATEX COATING AND METHOD OF MAKING THE SAME

(75) Inventors: Terrence B. Mazer, Reynoldsburg; Joseph E. Walton, Westerville; Barbara S. Arnholt, Worthington; Monty L. Evans, Johnstown; Ronita K. Geckle, Columbus; Daniel Hamilton, Plain City; John J. Kropczynski, Jr., Dublin; Frank A. Murawski, Westerville; Larry G. Tucker, Powell; Sherri A. Walker, Sunbury; Michael V. Walsh, Westerville; Rhonda Cole Walsh, Westerville, all of OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/345,915

(22) Filed: Jul. 1, 1999

(51) Int. Cl.$^7$ .................................................... A61K 9/30

(52) U.S. Cl. ...................... 424/480; 424/464; 424/468; 424/472; 424/474; 424/475

(58) Field of Search ................................ 424/468, 464, 424/472, 473, 474, 475, 480

(56) References Cited

U.S. PATENT DOCUMENTS

| | | |
|---|---|---|
| 3,760,984 | 9/1973 | Theeuwes . |
| 3,854,480 | 12/1974 | Zaffaroni . |
| 3,921,636 | 11/1975 | Zaffaroni . |
| 3,948,254 | 4/1976 | Zaffaroni . |
| 3,993,072 | 11/1976 | Zaffaroni . |
| 3,993,073 | 11/1976 | Zaffaroni . |
| 3,995,631 | 12/1976 | Higuchi et al. . |
| 4,008,719 | 2/1977 | Theeuwes et al. . |
| 4,177,256 | 12/1979 | Michaels et al. . |
| 4,200,098 | 4/1980 | Ayer et al. . |
| 4,285,987 | 8/1981 | Ayer et al. . |
| 4,832,690 | 5/1989 | Kuu . |
| 4,838,862 | 6/1989 | Baker et al. . |
| 4,839,281 | 6/1989 | Gorbach . |
| 4,874,365 | * 10/1989 | Frederick et al. ..................... 604/54 |
| 4,927,411 | 5/1990 | Pastrone et al. . |
| 4,968,507 | * 11/1990 | Zentner et al. ..................... 424/465 |

(List continued on next page.)

FOREIGN PATENT DOCUMENTS

| | | |
|---|---|---|
| 0 425 023 | 5/1991 | (EP) . |
| 93/02558 | 2/1993 | (WO) . |
| 96/21478 | 7/1996 | (WO) . |
| 98/03161 | 1/1998 | (WO) . |

* cited by examiner

*Primary Examiner*—Thurman K. Page
*Assistant Examiner*—P. E. McQueeney
(74) *Attorney, Agent, or Firm*—David L. Weinstein; Daniel J. Hulseberg

(57) ABSTRACT

Dosage form unit is provided to deliver one or more beneficial agents into a fluid, such as liquid enteral nutritional product. The dosage form unit includes a core containing at least one beneficial agent, preferably a marker dye, which is dispersible in the fluid. The core also contains a compatible binding agent to bind the beneficial agent together. Additional components of the core may include a plasticizer, a standard flow agent, a lubricant, additional tableting aids and at least one hydrophilic agent. A latex coating encases the core. The latex coating includes a mixture containing a substantially hydrophobic base material, preferably formed from an emulsion of cellulose acetate microspheres, which is capable of defining a matrix-type membrane, and at least one hydrophilic component being dispersible in the fluid. A dispersible beneficial agent is preferred as one of the hydrophilic components of the latex coating to allow immediate release of the beneficial agent therefrom. A method of making the dosage form unit also is provided.

4 Claims, 5 Drawing Sheets

U.S. PATENT DOCUMENTS

| | | |
|---|---|---|
| 4,983,399 | 1/1991 | Maish . |
| 5,160,742 | 11/1992 | Mazer et al. . |
| 5,162,057 * | 11/1992 | Akiyama et al. .................... 106/243 |
| 5,318,558 | 6/1994 | Linkwitz et al. . |
| 5,324,280 | 6/1994 | Wong et al. . |
| 5,348,746 | 9/1994 | Dong et al. . |
| 5,358,721 | 10/1994 | Guittard et al. . |
| 5,413,777 * | 5/1995 | Sheth et al. .......................... 424/490 |
| 5,451,409 | 9/1995 | Rencher et al. . |
| 5,531,681 | 7/1996 | Walton et al. . |
| 5,531,682 | 7/1996 | Mazer et al. . |
| 5,531,734 | 7/1996 | Geckle et al. . |
| 5,531,736 | 7/1996 | Wong et al. . |
| 5,533,973 | 7/1996 | Piontek et al. . |
| 5,549,550 | 8/1996 | Mazer et al. . |
| 5,681,582 * | 10/1997 | Gilis et al. .......................... 424/468 |
| 5,738,651 | 4/1998 | Walton et al. . |
| 5,741,243 | 4/1998 | Geckle et al. . |
| 5,746,715 | 5/1998 | Mazer et al. . |
| 5,755,688 | 5/1998 | Piontek et al. . |
| 5,755,689 | 5/1998 | Mazer et al. . |

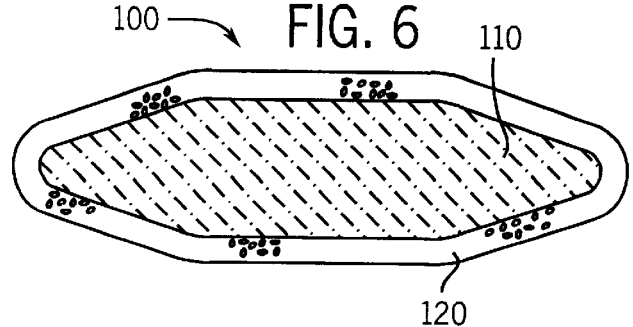
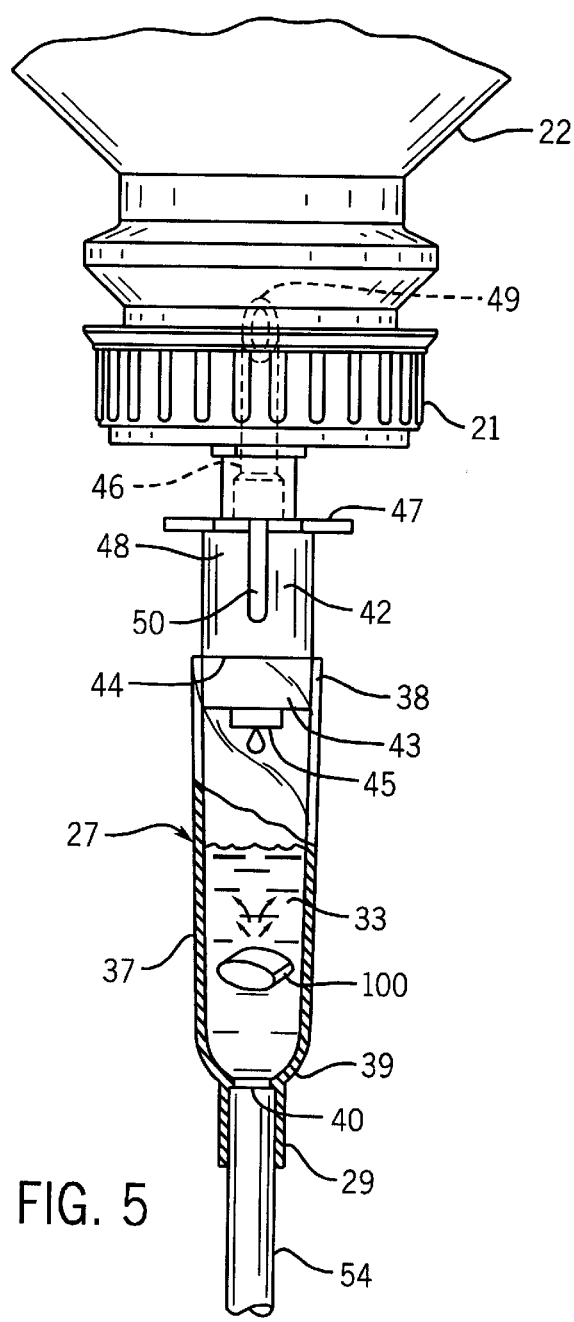

SUSTAINED RELEASE DOSAGE FORM UNIT HAVING LATEX COATING AND METHOD OF MAKING THE SAME

FIELD OF THE INVENTION

The invention relates to a coating system for sustained release of a beneficial agent from a dosage form, and particularly to a dosage form unit having a latex coating for sustained release of a beneficial agent such as a marker dye into a liquid enteral nutritional product. The invention further relates to a method of making and using the sustained release dosage form unit.

BACKGROUND OF THE INVENTION

A variety of devices and methods are known for the enteral, parenteral or oral delivery of beneficial agents, such as nutrients, medicaments, probiotics, diagnostic agents and marker dyes, to a patient. For example, it is well known to feed a fluid, such as a liquid enteral nutritional product, by gravitational or positive flow from a hangable bottle or bag having an outlet connected to a drip chamber which, in turn, is connected to a flexible tubing or lumen leading to a nasogastric tube or a feeding tube inserted through a gastrostomy or a jejunostomy to a patient. The liquid enteral nutritional product may be aseptically processed or terminally retorted, and may be supplied in a pre-filled, ready-to-hang container, or placed in such a container by a caregiver. However, the selection of diets, particularly special diets, from amongst the rather modest number of typically available liquid enteral nutritional products that are currently available is rather limited.

Moreover, it is often desirable to administer simultaneously a variety of beneficial agents, such as nutrients, medicaments, probiotics, diagnostic agents and marker dyes. These various ingredients, however, often are not stable during heat sterilization and may not be mutually compatible with other desired ingredients for an extended period of time, such as days or even months until used. As such, the combination of these beneficial agents are not readily amenable to large scale preparation and consequent storage as the product moves through commerce.

It also is beneficial to make the liquid enteral nutritional product more detectable in a patient after delivery, such as for diagnostic purposes and to identify when the enteral nutritional product is improperly fed to an area external to the stomach or intestines. One such method of making the liquid enteral nutritional product more detectable is to dissolve a suitable physiologically acceptable marker dye into the liquid product. Because compatibility of such marker dyes with other beneficial agents must be considered, it is advisable not to introduce the marker dye prior to heat sterilization or extended storage.

For these reasons, it therefore has been desirable to alter, modify or mark nutritional products during enteral tube feeding into the gastrointestinal tract of a patient. Certain new apparatus and methods have been developed to address these needs, and are the subject of several recent patents, including U.S. Pat. No. 5,531,681, U.S. Pat. No. 5,531,682, U.S. Pat. No. 5,531,734, U.S. Pat. No. 30 5,533,973, U.S. Pat. No. 5,549,550, U.S. Pat. No. 5,738,651, U.S. Pat. No. 5,741,243, U.S. Pat. No. 5,746,715, U.S. Pat. No. 5,755,688, and U.S. Pat. No. 5,755,689. Generally, these patents are directed to various aspects of apparatus and methods, which use a formulation chamber joined in fluid communication with a feeding device, and a dosage form unit placed within the formulation chamber. The dosage form unit contains the desired beneficial agents to be added to the liquid enteral nutritional product. As noted by the identified patents, a variety of dosage form units are available for use with these apparatus and methods, including conventional osmotically-driven delivery devices for sustained delivery of a beneficial agent.

One such osmotic delivery device is disclosed in U.S. Pat. No. 5,318,558, which is directed to a pump-type, controlled-release dosage form unit, or delivery device. Generally, the device includes a cylindrical enclosure containing the beneficial agent at one end portion and a piston driven by an osmotic engine at the other end portion. A small orifice is formed in the enclosure, preferably by a laser beam drill, at the end opposite the osmotic engine. In this manner, the beneficial agent is forced from the enclosure through the orifice upon activation of the osmotic piston.

An alternative osmotic dosage system with a sustained release dosage is disclosed by U.S. Pat. No. 5,324,280, wherein the beneficial agent is enclosed within an inner wall surrounded by a layer of hydro-active material that is entirely confined within an outer wall. Osmotic pressure resulting from expansion of the hydro-active material forces the beneficial agent out through a passageway formed in the outer wall by a laser drill or the like.

As noted, each of these conventional osmotic drug delivery devices requires that an orifice or similar passage be drilled or otherwise preformed in an outer membrane. Such precision manufacturing techniques, however, can be both difficult and expensive to perform. Additionally, it has been found that such conventional osmotic drug delivery devices are not particularly efficient, especially when used for the delivery of a marker dye or the like.

Furthermore, it is often desirable to provide an immediate release of beneficial agent upon initial exposure to the liquid enteral nutritional product. To accomplish this immediate release, conventional osmotic delivery systems typically require that an outer layer or film of the desired beneficial agent be provided. In this manner, an initial amount of the beneficial agent can be released quickly upon dispersion within the liquid nutritional product, followed by a sustained release of the beneficial agent from the dosage form unit. The provision of an additional outer film of beneficial agent, however, increases the manufacturing and material costs of the drug delivery device.

As such, there remains a need for an improved dosage form unit capable of sustained delivery of the beneficial agent(s) contained therein.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied and broadly described, the invention includes a dosage form unit to deliver a beneficial agent into a fluid. Particularly, and as embodied herein, an intended use of the dosage form unit is for delivering one or more beneficial agents into a liquid enteral nutritional product to be fed to the gastrointestinal tract of a patient.

The dosage form unit of the invention includes a core containing at least one beneficial agent, which is dispersible in a fluid, such as liquid enteral nutritional product. As embodied herein, the beneficial agent is selected from a group consisting of nutrients, medicaments, probiotics, diagnostic agents and, in the preferred embodiment, marker dyes. Particularly, F.D.&C. Blue Dye #1 and methyl anthranilate are two such preferred markers.

The core also contains a compatible binding agent to bind the beneficial agent together. Although a variety of binding agents may be used, cellulose acetate is preferred. In the preferred embodiment, a plasticizer or cold solvent such as triacetin is used to soften the cellulose acetate and thus enhance binding to establish a stronger core. If desired or necessary, a conventional lubricant and a standard flow agent also can be provided for construction of the core. Other known tableting aids also may be used, such as dicalcium phosphate, to enhance the core construction. The core embodied herein also includes at least one hydrophilic agent, such as hydroxypropyl methylcellulose, and one or more osmotically effective compounds if desired, to create an osmotic system for delivery of the beneficial agent.

Further in accordance with the present invention, the dosage form unit also includes a latex coating encasing the core. The latex coating includes a mixture containing a substantially hydrophobic base material capable of defining a semi-porous matrix-type membrane and at least one hydrophilic component being dispersible in the fluid. Preferably, the base material of the latex coating is formed from an emulsion of cellulose acetate microspheres.

A variety of hydrophilic components can be used for the latex coating, provided such components are dispersible in the fluid of interest, so as to create or open passages in the matrix-type membrane defined by the base material of the latex coating. A preferred hydrophilic component is polyethylene glycol, which not only facilitates the formation of passages, but also increases the flexibility of the wall formed by the latex coating and increases fluid-flux therethrough. If the immediate release of a beneficial agent is desired upon contact of the dosage form unit with a fluid, it is further preferred that the beneficial agent be provided as a component of the latex coating. This beneficial agent of the latex coating preferably is selected from a group consisting of nutrients, medicaments, probiotics, diagnostic agents and marker dyes.

In this manner, the dosage form unit may be configured to be placed within the formulation chamber of an enteral feeding system. Preferably, the dosage form unit is shaped so as to inhibit blockage of the enteral feeding system, such as in the shape of a square tablet.

The present invention also is directed to a method of forming a dosage unit to deliver a beneficial agent into a fluid, such as a liquid enteral nutritional product. The method includes the step of forming a core containing at least one beneficial agent dispersible in a fluid and a compatible binding agent to bind the beneficial agent together. As previously noted, the beneficial agent is selected from a group consisting of nutrients, medicaments, probiotics, diagnostic agents and, preferably, marker dyes, whereas the binding agent is cellulose acetate softened with triacetin. Likewise, the forming step can include adding a standard flow agent, a lubricant, or other tableting aids to the core. The method further includes, in the preferred embodiment, adding at least one hydrophilic agent, such as hydroxypropyl methylcellulose, and one or more osmotically effective compounds if desired to the core.

Further in accordance with the invention, the method also includes the step of preparing a latex formulation including a mixture containing an emulsion of a substantially hydrophobic base material capable of defining a matrix-type membrane and at least one hydrophilic component dispersible in the fluid. This step preferably includes mixing an emulsion of cellulose acetate as the base material with the hydrophilic component. Although other hydrophilic components may be provided, an additional aspect of the invention includes providing a beneficial agent dispersible in the fluid as a component of the latex formulation, so as to facilitate immediate release of the beneficial agent upon exposure of the dosage form unit to the fluid. This beneficial agent for the latex formulation is preferably selected from a group consisting of nutrients, medicaments, probiotics, diagnostic agents and marker dyes.

Finally, the method of the invention includes applying the latex formulation onto the core to form a latex coating thereon. Preferably, this step is performed by spraying the latex formulation onto the core using a conventional pan coater or a Wurster column in a batch fluid bed coater as is known in the art, and then drying the applied coating to define an outer wall.

Other features and advantages of the present invention will become readily apparent from the following detailed description, the accompanying drawings, and the appended claims.

The accompanying drawings, which are incorporated in and constitute part of this specification, are included to illustrate and provide a further understanding of the method and system of the invention. Together with the description, the drawings serve to explain the principles of the invention.

BRIEF DESCRIPTION OF THE DRAWINGS

The present invention will be better understood with reference to the appended drawings in which:

FIG. 5 is an enlarged fragmentary view of a formulation chamber for feeding a liquid enteral nutritional product to a patient with the dosage form unit of the present invention placed therein; and FIG. 6 is an enlarged cross-sectional view of the representative embodiment of the dosage form unit of the present invention shown in FIG. 5.

DEFINITIONS USED

Figure 1:
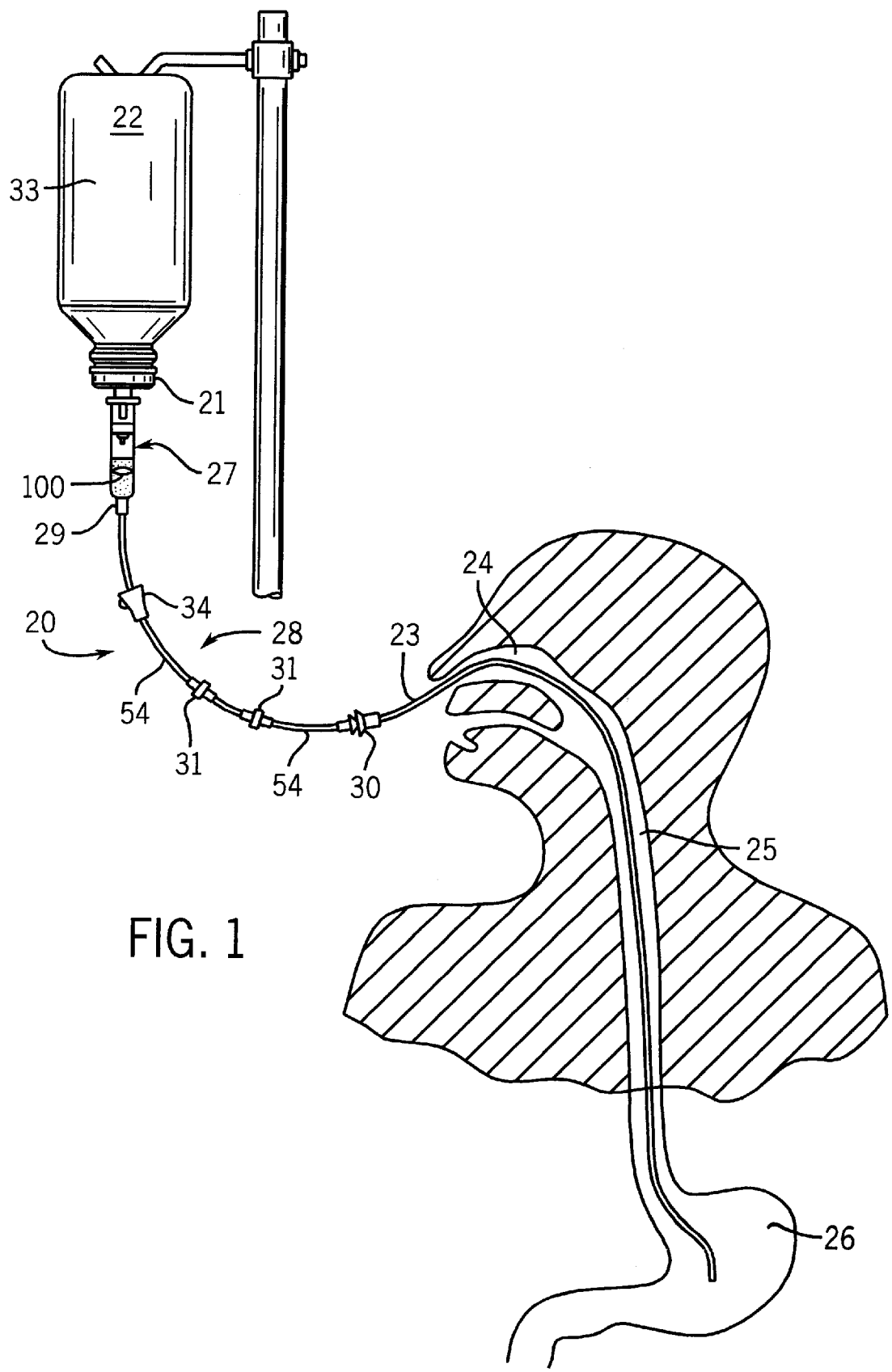
FIG. 1 is a schematic representation of an apparatus for modification or marking of a liquid enteral nutritional product for nasogastric feeding to a patient.

The following terms and phrases are defined for the purposes of the description and claims.

"Liquid enteral nutritional products" refers to liquid compositions commonly understood to be supplied to and utilized in the gastrointestinal tracts of patients. Such enteral nutritional products have a viscosity in the range of 1 to about 300 cps. and more likely at least about 3 cps., but most frequently in the range of about 5 to about 150 cps.

"Enteral nutritional product medium" refers to the liquid portion of a liquid enteral nutritional product, mainly water, but often including lesser or minor amounts of one or more liquid non-aqueous substances such as lipids, e.g., vegetable oil and marine oil.

The term "gastrointestinal tract" as used herein refers to the stomach and the small bowel. Feeding to the gastrointestinal tract is performed by use of a nasogastric tube extending through a nasal passage and the esophagus and thence to the stomach, or by use of a feeding tube extending through the abdominal wall to the stomach or small intestine.

A "physiologically significant agent" or "beneficial agent" is an agent or ingredient that is, or is believed to be, nutritionally or pharmaceutically important to the patient, such as nutrients and medicaments, or is otherwise medically important as in the case of a probiotic or a diagnostic agent, such as a marker dye.

A "probiotic" is understood to be a live microbial food supplement which beneficially affects the human host by improving the individual's microbial balance in the gastrointestinal tract, e.g., Lactobacillus reuteri.

A "beneficial agent or ingredient dispersible in a fluid or liquid enteral nutritional product" is an agent or ingredient that is physiologically beneficially added, or otherwise usefully beneficially added, as in the case of a diagnostic agent or marker dye, to the fluid or liquid nutritional product during enteral feeding, so as to be dispersible therein. The beneficial agent(s) or ingredient(s) are dispersible in the liquid enteral nutritional product being modified during feeding, so as to be carried along with the nutritional product into the gastrointestinal tract of the patient.

A "useful amount" of a beneficial agent that is dispersible in the medium of the liquid enteral nutritional product is an amount that is "physiologically effective or diagnostically detectable" with respect to a patient; i.e., it produces, or is reasonably expected to produce, a detectable beneficial effect on the patient on either a short term or long term basis when fed as part of a liquid enteral nutritional product, or, is detectable in diagnosing a condition or disease. Generally not more than about 5 grams of beneficial agent will be contained in a single sustained release dosage form unit or device, and a plurality or even multiplicity of units containing a given beneficial agent may be employed to provide a desired level of the beneficial agent in the nutritional product being fed.

The phrase "at least one beneficial agent dispersible in the medium of the liquid enteral nutritional product" is meant to refer to the singular as well as the plural, as may well be adjudged from the context, and includes combinations of ingredients, agents or factors.

The term "dispersible" as used herein with respect to beneficial agent(s) or ingredient(s) is to be understood to apply to substances that are soluble as well as those that are sufficiently suspendable to be taken up readily and carried along by a fluid, such as a liquid enteral nutritional product flowing through a formulation chamber containing one or more sustained release dosage form units.

The term "feeding set" refers to the combination of one or more formulation chambers, such as a drip chamber, and fluid communication means leading to a feeding tube for enteral feeding. Each formulation chamber may be loaded with or accompanied by at least one dosage form unit containing a useful amount of at least one beneficial agent, such as a marker dye.

The process of "infusion" is meant to refer, in the present context, to the process of supplying an enteral-soluble beneficial ingredient to the gastrointestinal tract of a patient extending over time from at least a minute to about 30 hours, but more usually at least about 2 hours to about 24 hours.

The term "delivery system" or "delivery device" denotes generically a means or system for storing and subsequently delivering or releasing a beneficial ingredient or agent or mixture thereof into a fluid, such as a liquid enteral nutritional product flowing through a formulation chamber.

The term "a sustained release dosage form" as used herein with regard to the present invention, refers to a form of device that stores and subsequently releases or disperses a useful amount of a beneficial agent into the medium of a fluid, such as liquid enteral nutritional product, at room temperature more slowly than the rate normally exhibited by the solubility characteristics of that beneficial agent, when in uncoated or untreated particulate form and in the same medium at the same temperature. Generally, the sustained release dosage form exhibits dissolution or dispersion during the course of at least 30 minutes, and preferably at least two hours, during contact by the flowing fluid or liquid enteral nutritional product. As to a beneficial agent that inherently is not promptly soluble in the medium of a liquid enteral nutritional product, the sustained release dosage form unit retards delivery of the beneficial agent by at least 20 percent of the normal time for solubilization or dispersion into the medium of a liquid enteral nutritional product. Preferably, the sustained release dosage form unit prolongs the release of the contents thereof for a time appropriate to the nutrient or medicament or other beneficial agent being supplied.

The term "sustained release dosage form units" refers to individual coated tablets or devices capable of the sustained delivery of beneficial agent, such as marker dye, as defined above.

It also is noted that the phrase "flowing liquid enteral nutritional product through the apparatus" is meant to include utilizing gravity flow from a container, as well as using a pump with or without gravity flow to promote the flow of the liquid enteral nutritional product through a feeding tube.

DETAILED DESCRIPTION OF THE INVENTION

To better understand the manner in which the dosage form unit of the present invention may be used, reference is first made to the apparatus and methods of modifying and marking liquid enteral nutritional products and the like as set forth in U.S. Pat. No. 5,531,681, U.S. Pat. No. 5,531,682, U.S. Pat. No. 5,531,734, U.S. Pat. No. 5,533,973, U.S. Pat. No. 5,549,550, U.S. Pat. No. 5,738,651, U.S. Pat. No. 5,741,243, U.S. Pat. No. 5,746,715, U.S. Pat. No. 5,755,688, and U.S. Pat. No. 5,755,689. The specification and drawings of each of these identified patents is incorporated herein by reference. It should be understood that apparatus and methods of each of these identified patents allow for beneficial agents, including marker dyes, to be delivered from any of a variety of dosage forms, whether or not in controlled release dosage form. For purpose of the present invention, however, reference is made specifically to a sustained released dosage form unit. Various embodiments of the apparatus and methods disclosed therein are summarized as follows for purpose of illustration and not limitation.

Figure 3:
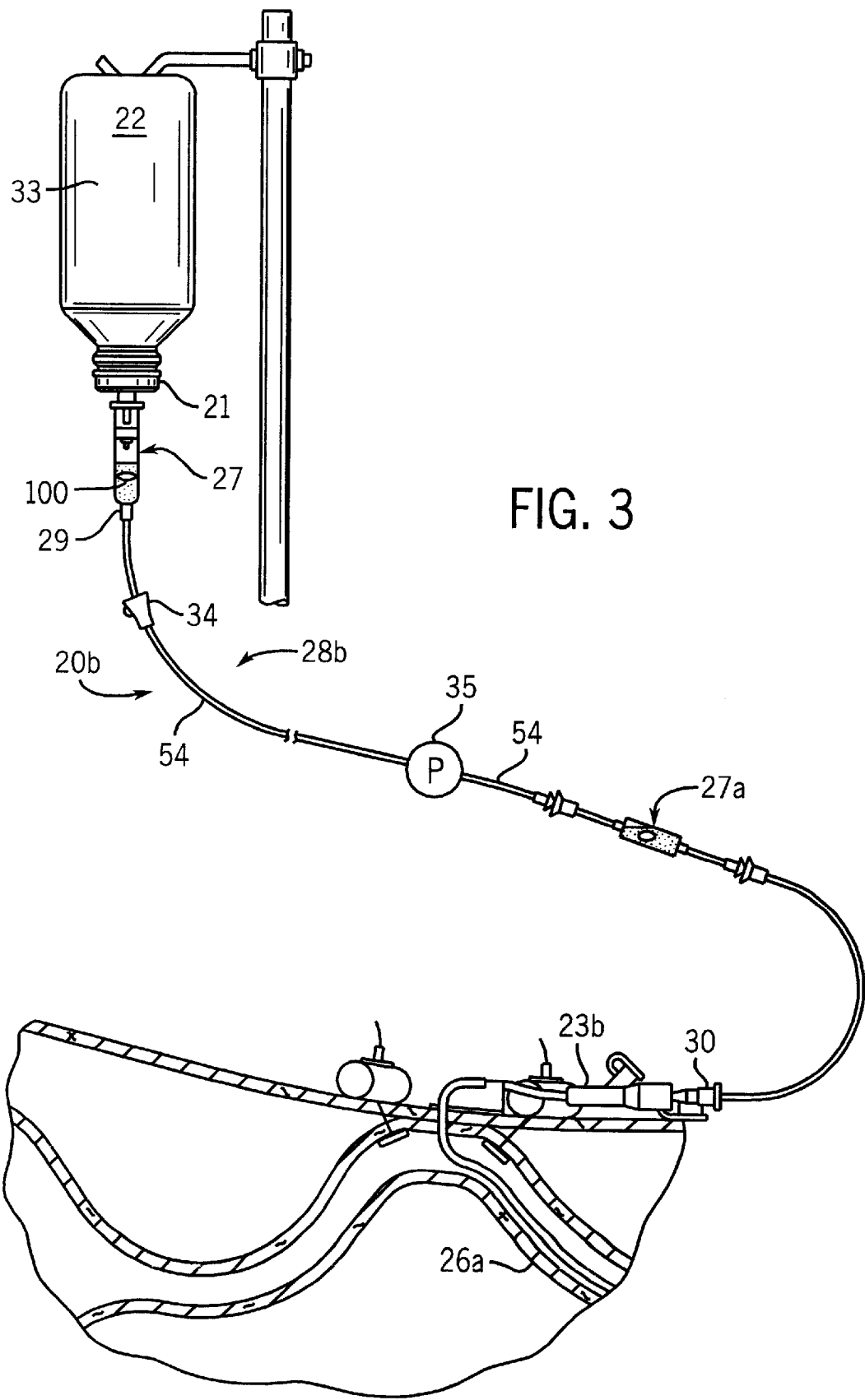
FIG. 3 is a schematic representation of an apparatus, including two formulation chambers provided in series, for modification or marking of a liquid enteral nutritional product for jejunostomic feeding to a patient.
Figure 4:
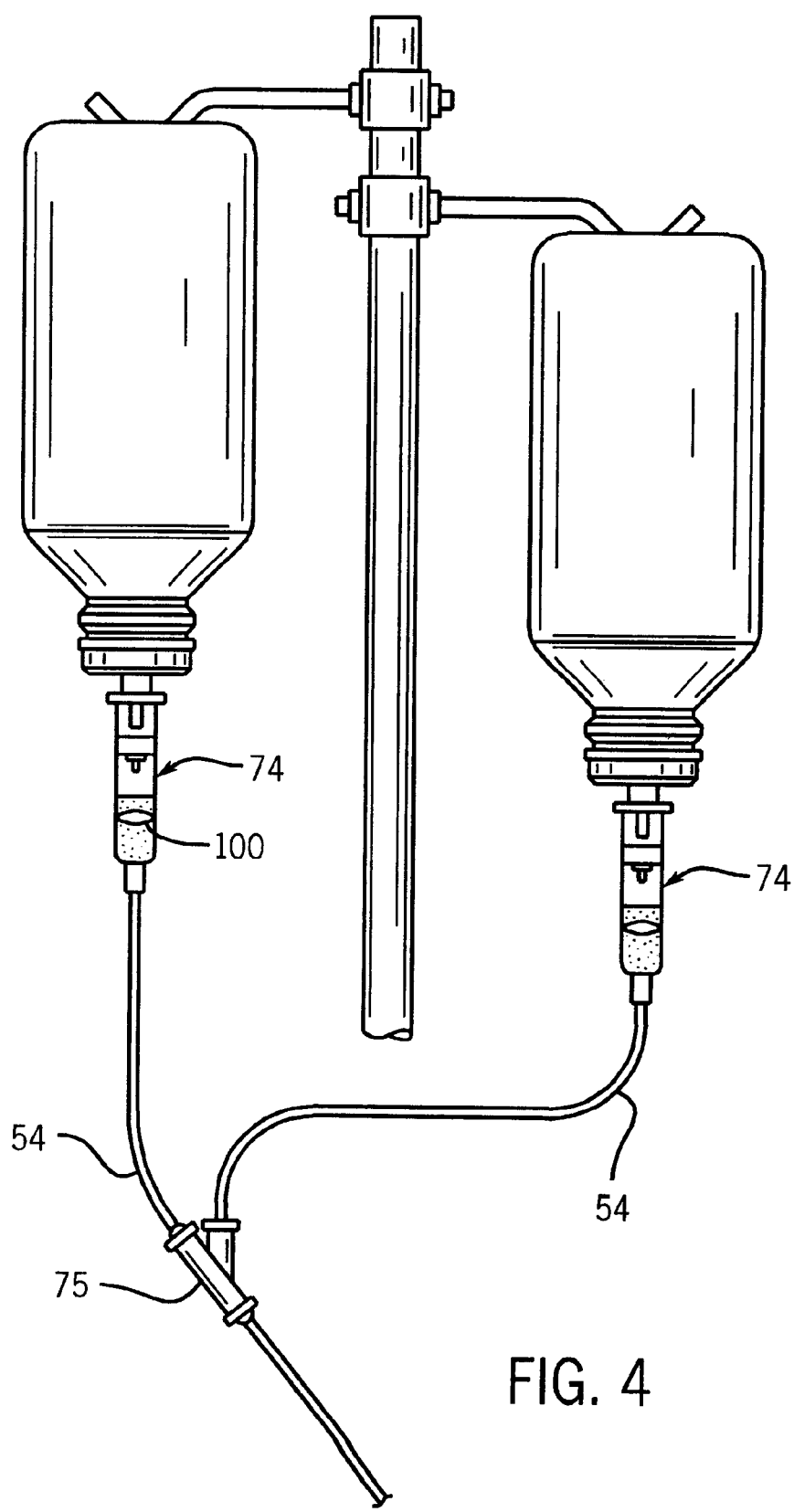
FIG. 4 is a partial schematic representation of an apparatus having two formulation chambers connected in parallel for modifying or marking a liquid enteral nutritional product.

FIG. 1 shows a feeding set, indicated generally by reference character 20, connecting outlet 21 of hanging supply container 22 to nasogastric feeding tube 23 that extends through nasal passage 24 of the patient and down esophagus 25 to stomach 26. The feeding set here consists of formulation chamber 27, in the form of a drip chamber, 10 and fluid communication means indicated generally by reference character 28. "Fluid communication means" is to be understood to include all components of fluid communication utilized in series from drip chamber outlet 29 to connection 30 to the feeding tube, such as nasogastric feeding tube 23. Components include not only portions of flexible tubing 54 but also any additional drip chambers or other formulation chambers connected in series as shown in FIG. 3, or in parallel as seen in FIG. 4. The components may also include any special tubing portions needed for utilization of a pump, and, connector elements, respectively, between all the other components, such as connector elements 31 or adapters 30.

Referring again to FIG. 1, formulation chamber 27 has positioned therein a sustained release dosage form unit 100 in accordance with the present invention. The dosage form unit 100 contains a physiologically effective or diagnostically detectable amount of at least one beneficial agent dispersible in a fluid, such as liquid enteral nutritional product 33 flowing from supply container 22 into formulation chamber 27. The liquid enteral nutritional product, as embodied herein, is normally water-based and contacts controlled release dosage form unit 100. Upon exposure to the fluid or liquid enteral nutritional product, the beneficial agent or agents is released or delivered into the fluid. The flow of liquid enteral nutritional product can be conveniently controlled by the use of a conventional adjustable compression clamp 34.

Figure 2:
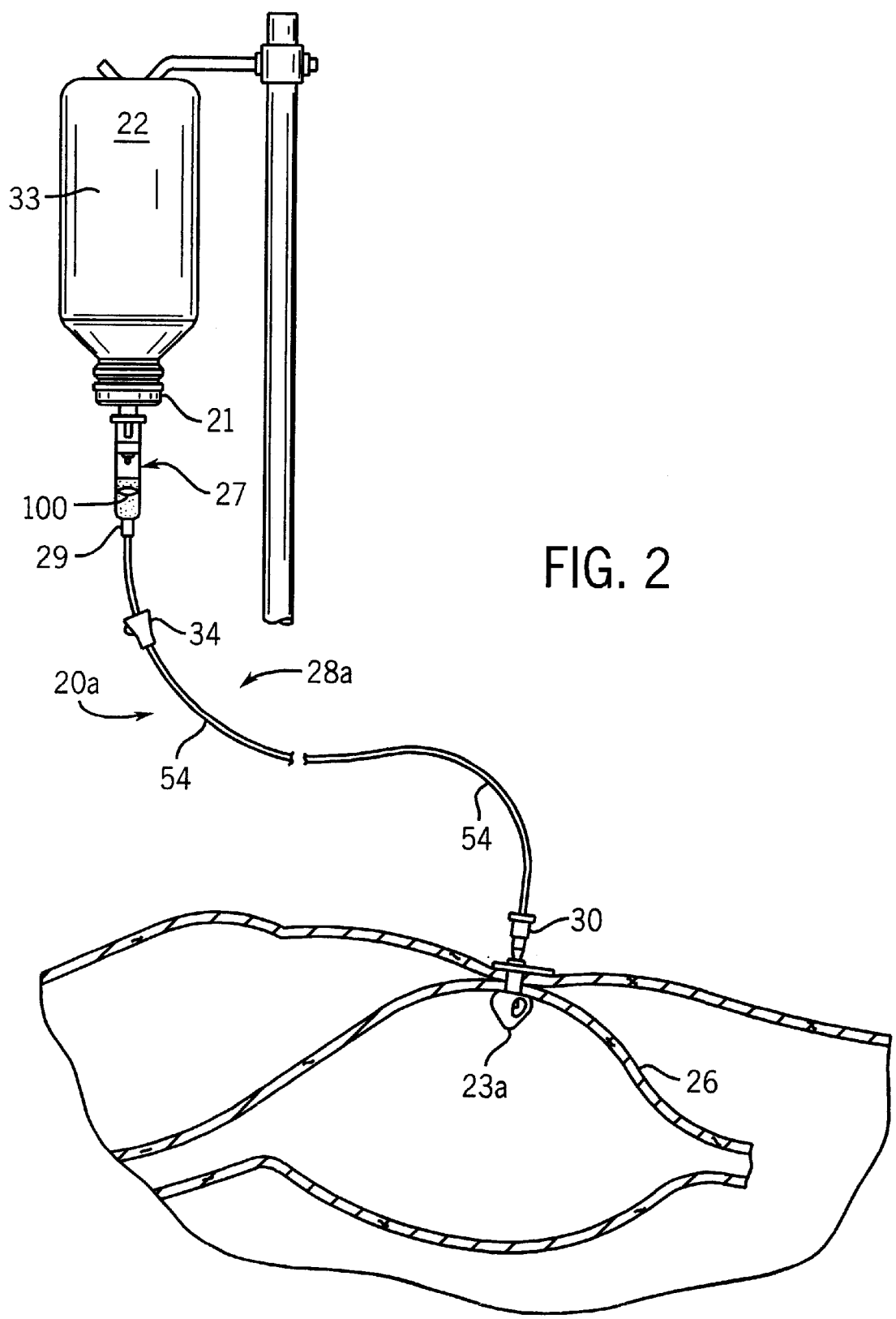
FIG. 2 is a schematic representation of an apparatus for modification or marking of a liquid enteral nutritional product for gastrostomic feeding to a patient.

FIG. 2 shows a hanging supply container 22 supplying liquid enteral nutritional product 33 to formulation chamber 27 and into flexible tubing 54 of feeding set 20a to the gastrostomy feeding tube device 23a. The gastrostomy feeding tube device shown in FIG. 2 is merely exemplary of one of many devices that are commercially available and suitable for use with the invention.

FIG. 3 is directed to a feeding arrangement for a jejunostomy much like the apparatus in FIG. 1, except that feeding set 20b is adapted to be used with a pump 35 for positive flow into feeding tube 23b leading to small bowel 26a of the patient. An example of a suitable pump is disclosed in U.S. Pat. No. 4,927,411. A second formulation chamber 27a also may be employed as part of feeding set 20b, as shown, in order to add additional or different beneficial agents, each dispersible in the fluid, such as liquid enteral nutritional product 33 flowing from supply container 22 to formulation chamber 27 and thence through the remainder of the communication means 28b and formulation chamber 27a of feeding set 20b to jejunostomy feeding tube 23b. The additional beneficial agent may be in controlled or non-controlled dosage form.

Reference is now made in detail to a present preferred embodiment of the invention, an example of which is illustrated in the accompanying drawings. The method and corresponding steps of the invention will be described in conjunction with the detailed description of the dosage form unit.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

In the enlarged fragmentary view in FIG. 5, a sustained release dosage form unit 100 of the present invention is placed in a liquid enteral nutritional composition 33 within the formulation chamber 27. As shown, the sustained release dosage form unit 100 is provided with a suitable geometric shape, such as a rectangular solid, to prevent blocking the flow of the liquid enteral nutritional product 33 through the formulation chamber. Although a generally square-shaped tablet is shown, any of a variety of alternative shapes likewise may be used. Additionally, the formulation chamber may be provided with a mesh sleeve or similar device to further inhibit such blockage.

For purpose of illustration, and not limitation, FIG. 6 shows a cross-sectional view of a representative embodiment of the dosage form unit of the present invention. In accordance with the present invention, and as shown in FIG. 6, the dosage form unit 100 includes a core 110 containing at least one beneficial agent dispersible in a fluid and a compatible binding agent to bind the beneficial agent together. The dosage form unit 100 further has a latex coating 120 encasing the core 110, wherein the latex coating 120 includes a mixture containing a substantially hydrophobic base material capable of defining a matrix-type membrane and at least one hydrophilic component dispersible in the fluid. The construction of the sustained release dosage form unit of the present invention, as embodied herein, will now be described in detail.

Construction Of The Core

In accordance with the present invention, the sustained released dosage form unit generally includes a core containing at least one beneficial agent. For simplicity, it is understood that the term "beneficial agent" refers to both the singular and the plural, unless otherwise noted. Any of a variety of beneficial agents may be used within the scope of this invention, provided each beneficial agent is dispersible, and preferably hydrophilic or soluable, within the fluid, e.g., liquid enteral nutritional product, within which it is to be exposed.

For example, the beneficial agents that are likely to be added to conventional enteral nutritional compositions include nutrients, such as, glutamine, arginine, fermentable dietary fibers, non-fermentable dietary fibers, enzymes such as lipases, combinations of amino acids, oligosaccharides such as fructo-oligosaccharides, vitamins, short chain ($C_3$–$C_4$) fatty acids, pyruvate precursors the form of pyruvamide, or pyruvyl-amino acids, such as, pyruvyl-glycine, pyruvyl-alanine, pyruvyl-leucine, pyruvyl-valine, pyruvyl-sarcosamine and their amides, esters and salts, structured lipids, d-cyroinositol, lactoferrin, marine oils and acidulents such as ascorbic acid. An example of a structured lipid which provides excellent nutritional support is a glycerol backbone with at least one gamma linolenic acid or dihomogamma-linolenic acid residue in combination with a medium chain ($C_5$–$C_{22}$) fatty acid residue and a $C_{18}$–$C_{22}$ n-3 fatty acid residue selected from alpha-linolenic and stearodonic, eicosapentaenoic and docosahexaenoic acid.

Medicaments that may be usefully administered in accordance with the present invention if sufficiently dispersible include, for example, antihistamine drugs, anti-infective agents, such as antibiotics, antivirals and urinary tract anti-infectives, antineoplastic agents, autonomic drugs such as adrenergic agents and skeletal muscle relaxants, blood formation and coagulation drugs, cardiovascular drugs, central nervous system agents, diagnostic agents, electrolytic, caloric and water balance agents, enzymes, antitussive, expectorant and mucolytic agents, gastrointestinal drugs such as antacids, gold compounds, hormones and synthetic substitutes, smooth muscle relaxants, and unclassified therapeutic agents. Other examples are $H_2$ blockers like Tagamet®, prokinetic medication, bioactive peptides, medication for diabetic condition, chemotherapy agents, or any medication intended for oral administration that will not react adversely with the nutritional formulation being fed into the gastrointestinal tract.

Probiotics that may be usefully administered in accordance with the invention if sufficiently dispersible include, for example, *Lactobacillus acidophilus* GG, as described in U.S. Pat. No. 4,839,281, *Lactobacillus reuteri, Lactobacillus animalis*, and *Lactobacillus salivarius*, as described in WO 93/02558. Probiotics are live microorganisms that aid in the digestion of food or that help control the population of harmful microorganisms in the intestines.

In a preferred embodiment of the invention, the beneficial agent contained within the core is a physiologically acceptable marker dye or dye mixture. For example, a marker dye or dye mixture that is useful according to the invention is a colorant dye or a fluorescent dye or a mixture of such dyes that is physiologically acceptable to the patient and compatible with the other beneficial agents being fed therewith. Preferably, the dye or dye mixture also is capable of being delivered from the core in detectable concentrations in the liquid enteral nutritional product while the product flows through the formulation chamber. If the dye is detectable in the formulation chamber, it can be expected to be detectable, ordinarily, if it somehow reaches the oral cavity of the patient.

The marker dye employed may be a colorant dye that imparts color that is visible under white light, for example, normal daylight or artificial room light encountered in a hospital or clinic, or, the marker dye may be a fluorescing dye that fluoresces visibly under ultraviolet light, or, the marker dye may be a mixture of a colorant dye and a fluorescing dye. A mixture of a colorant dye and fluorescing dye appears to be especially advantageous in that flow through the formulation chamber is readily perceived under normal lighting conditions with colorant dye present, while even a small amount of nutritional product out of place, for example, in the oral cavity or nasal passage, will be more easily detected with the aid of ultraviolet light if it contains a fluorescing dye. This is because of the nature of the fluorescing dyes that are especially visible under ultraviolet light even when present in very low concentration.

The dye or dye mixture used must be physiologically acceptable. Usually food grade colorant dyes approved under the provisions of the United States Food, Drug and Cosmetic Act (F.D.&C.) are suitable. Preferred are F.D.&C. Blue #1 and F.D.&C. Blue #2 dyes, as further set forth below. The dye or dye mixture also must be dispersible in the liquid enteral nutritional product being fed, and compatible with the other beneficial agents being added during the feeding, if any. Generally about 0.06 milligram of dye per milliliter of liquid enteral nutritional product is desired to give a readily visible coloration to the nutritional product.

Wherein it is important to be able to detect misdirected liquid enteral nutritional product, the marker dye used may be a fluorescing dye, such as F.D.& C. Red Dye #3, which is highly visible at a very low concentration under ultraviolet light and also imparts a visible coloration to the liquid nutritional product under white light conditions. Other suitable fluorescing dyes are: quinine, F.D.& C. Red #22, F.D.& C. #28, fluorescein, and D 282 UV Blue available from DaGlo of Cincinnati, Ohio and also identified as 16470-24-9 in the Chemical Abstracts System with a color index of 220 as a fluorescent brightener. As indicated above, if desired, a mixture of colorant dye and fluorescing dye may be used. Generally, an amount sufficient to add about 0.01 to 0.05 mg/ml of fluorescing dye to the liquid nutritional product is adequate for detectability under ultraviolet light.

In accordance with an additional aspect of the invention a preferred beneficial agent is a fluorescent marker established from a flavor compound, i.e. a fluorescing flavor compound. A variety of such compounds are available including iso-butyl anthranilate, n-butyl anthranilate, allyl anthranilate, iso-butyl n-methyl anthranilate, allyl anthranilate, butyl anthranilate, isobutyl anthranilate, cinnamyl anthranilate, cyclohexyl anthranilate, ethyl anthranilate, linalyl anthranilate, methyl anthranilate, methyl n-methyl anthranilate, betanaphthyl anthranilate, phenethyl anthranilate, terpinyl anthranilate. The preferred compound, however, is methyl anthranilate, which is available as FEMA No. 2682.

Unless the beneficial agent itself has sufficient binding characteristics, the core also includes a binding agent or similar excipient. A wide range of suitable and physiologically compatible binding agents are known and available, the preferred binding agent depending upon the beneficial agent to be contained by the core. Examples of such binding agents or excipients include, but are not limited to, cellulose acylates, cellulose diacylates, cellulose triacylates, cellulose acetate, cellulose diacetate, cellulose triacetate, cellulose polymers including mono, di and tricellulose, alkanylates, alkenylates, and mono, di and tricellulose aroylates, cellulose propionate, cellulose acetate butyrate, cellulose triacylates such as cellulose trivalerate, cellulose trilanrate, cellulose tripalmitate, cellulose trisuccinate, and cellulose trioctanoate, cellulose diesters such as cellulose disuccinate, cellulose dipalmitate, cellulose dioctanoate, cellulose dipentanoate, and coesters of cellulose such as cellulose acetate butyrate, cellulose acetate propionate, cellulose isopropyl acetate, cellulose acetate pentanoate, as well as certain polypropylenes. As embodied herein for use with F.D.&C. Blue Dye #1, cellulose acetate available from Eastman Chemical Products under the designation CA-398-10NF is preferred to provide the core with increased durability and resistance to disintigration due to its lack of solubility.

Depending upon the binding agent or excipient selected, a plasticizer component typically is required to soften the binding agent into a workable form. Examples of known suitable plasticizer components include triethyl citrate, acetyltriethyl citrate, tri-n-butyl citrate, acetyltri-n-butyl citrate, dibutyl phthalate, diethyl phthalate, dibutyl sebacate, glyceryl triacetate, available from Eastman Chemical Products under the trade name of Eastman Triacetin, and acetylated monoglyceride, manufactured by Eastman Chemical Products under the trade name of Myvacet® 9-45. For use in combination with the selected cellulose acetate, triacetin is preferred for the core.

Additional tableting aids also may be used to enhance fabrication and construction of the core. For example, and as embodied herein, a standard flow agent, such as talc, colloidal silica, or kaolin, is included to prevent tackiness; wherein fumed silica commonly available under the trademark CAB-O-SIL from Cabot Corporation is preferred. A lubricant, such as calcium stearate, stearic acid or, preferably, magnesium stearate, also is provided for enhanced performance and construction of the core. Furthermore, stabilizers or similar substantially hydrophobic tableting aids such as dicalcium phosphate or lactose can be provided.

The core embodied herein also includes a hydrophilic agent to act as an acceptable carrier capable of assisting in delivery of the selected beneficial agent. Examples of various hydrophilic agents include hydrophilic polymers or osmopolymers, hydroxymethylcellulose, hydroxyethylcellulose, hydroxypropylcellulose, hydroxypropylmethylcellulose, hydroxyalkylcellulose, and hydroxypropylethylcellulose. In the preferred embodiment, hydroxypropyl methylcellulose (HPMC) is used due to its swelling characteristics as a result of imbibing the fluid or solvent to which it is exposed so as to facilitate osmotic delivery of the beneficial agent as will be further described.

Additionally, the core of the present invention also may include certain osmotically effective compounds, such as osmotically effective solutes or osmagents, in the core for enhanced performance of the osmotic system. Examples of possible osmotically effective compounds include sodium chloride, potassium chloride, magnesium chloride, potassium sulfate, sodium sulfate, lithium sulfate, potassium acid phosphate, mannitol urea, inositol, tartaric acid, raffinose, sucrose, glucose, sorbitol, and fructose.

The core can be manufactured with these components using standard techniques. For example, the various ingredients may be mixed into a solid, or a semisolid, by conventional methods such as mixing, blending, ballmilling, calendaring, stirring or rollmilling, and then pressed into a preselected core shape. The preferred method of manufacturing the dosage form unit, and thus the core, of the present invention is described in detail below.

Construction Of The Latex Coating

As previously noted, and in accordance with the present invention, the sustained dosage form unit also includes a latex coating to surround or encapsulate the core. As is well known, latex is generally recognized as an aqueous suspension of hydrocarbon polymer occurring naturally or an emulsion of a synthetic rubber or plastic obtained by polymerization. The latex coating is dried to form a semicontinuous structure; i.e., a structure substantially less continuous than that which would be formed by the same polymer or material applied via a solvent system. The coating thereby defines an outer wall of an osmotic system for delivery of the beneficial agent from the core as will be described in detail.

The latex coating embodied herein contains a mixture of a substantially hydrophobic base material and at least one hydrophilic component dispersible in a fluid, such as a liquid enteral nutritional product. In this manner, the hydrophilic component leaches or is otherwise disposed from the latex coating when the dosage form unit of the present invention is placed in contact with the liquid enteral product. The base material of the latex remains in the form of a semi-porous matrix-type membrane to allow delivery of the beneficial agent therethrough while containing the binding agent of the core.

A variety of substantially hydrophobic base materials may be used for the latex coating of the present invention. Such materials must be capable of suspension or emulsification, such as in water, and, when dried, define a matrix-type membrane capable of maintaining its integrity both before and after the hydrophilic component is leached therefrom. Examples of possible base materials include cellulose acylates, cellulose diacylates, cellulose triacylates, cellulose acetate, cellulose diacetate, cellulose triacetate, cellulose polymers including mono, di and tricellulose, alkanylates, alkenylates, and mono, di and tricellulose aroylates, cellulose propionate, cellulose acetate butyrate, cellulose triacylates such as cellulose trivalerate, cellulose trilanrate, cellulose tripalmitate, cellulose trisuccinate, and cellulose trioctanoate, cellulose diesters such as cellulose disuccinate, cellulose dipalmitate, cellulose dioctanoate, cellulose dipentanoate, and coesters of cellulose such as cellulose acetate butyrate, cellulose acetate propionate, cellulose isopropyl acetate, cellulose acetate pentanoate, as well as certain polypropylenes. As embodied herein, a cellulose acetate such as CA-398-10NF or CA-398-30NF from Eastman Chemical Products, is preferred. Particularly, the preferred embodiment of the dosage form unit is coated with a mixture containing a cellulose acetate emulsion available from FMC Corporation. This emulsion includes an aqueous suspension of cellulose acetate microspheres, between about 22–28% wt. and preferably between about 24–26% wt., having a size of between about 0.2 and 0.6 microns, but typically about 0.3 microns. The microspheres are suspended in water containing a wetting agent such as sodium laurel sulfate (2% wt.) or the like.

As previously noted, the hydrophilic components of the latex coating are provided, at least in part, to form passages through which the beneficial agent can be delivered from the core. Suitable hydrophilic components are soluble or otherwise capable of leaching from the matrix-type membrane of the base material when exposed to or placed in a fluid, such as liquid enteral nutritional product in the preferred embodiment. Examples of suitable hydrophilic components include lithium carbonate, sodium chloride, sodium bromide, sodium carbonate, potassium chloride, potassium sulfate, potassium phosphate, sodium benzoate, sodium acetate, sodium citrate, potassium nitrate, The alkaline earth metal salts such as calcium phosphate, calcium nitrate, calcium chloride, transition salts such as ferric chloride, ferrous sulfate, zinc sulfate, cupric chloride, manganese fluoride, manganese fluorosilicate, and the like, organic compounds such as polysaccharides including sucrose, glucose, fructose, mannitol, mannose, galactose, aldohexose, altrose, talose, sorbitol, and the like, organic aliphatic oils including diols and polyols, aromatic oils including diols and polyols, and the other polyols such as polyhydric alcohol, polyalkylene glycol, polyglycol, poly(a,w)-alkylenediols, and the like. The preferred embodiment includes maltodextrin as a hydrophilic component available under the tradername MALTRIN 100.

An additional hydrophilic component for the latex coating of the present invention embodied herein is polyethylene glycol (PEG) 3350, although other suitable PEG materials such as PEG 400 with different molecular weights can be used. The use of PEG material as a non-toxic hydrophilic material not only facilitates the formation of passages for the delivery of beneficial agent, but also is believed to increase the flexibility of the wall formed by the latex coating and increase aqueous fluid-flux therethrough. That is, PEG acts as a flux regulator to assist in regulating the fluid permeability or liquid flux through the outer wall defined by the latex coating.

As with the core, it is beneficial to provide a plasticizer or similar softening component for the latex coating of the present invention. Examples of known suitable plasticizer components include triethyl citrate, acetyltriethyl citrate, tri-n-butyl citrate, acetyltri-n-butyl citrate, dibutyl phthalate, diethyl phthalate, dibutyl sebacate, glyceryl triacetate, available from Eastman Chemical Products under the trade name of Eastman Triacetin, and acetylated monoglyceride, manufactured by Eastman Chemical Products under the trade name of Myvacet® 9-45., wherein triethyl citrate is preferred for the cellulose acetate of the latex coating embodied herein.

The use of a latex coating provides several advantages not available with conventional osmotic drug delivery systems. For example, the use of a latex material allows hydrophilic components to be dissolved or otherwise mixed readily into the aqueous emulsion prior to coating the core. As such, these hydrophyilic components eliminate the need to precision machine or laser drill pores or orifices in a solid outer wall as is typically performed for conventional osmotic devices. Additionally, the release rate of the beneficial agent from the core and through the wall can be controlled more readily by altering the hydrophilic components and quantities in the latex coating. That is, passage size and count can be increased by increasing the molecular size and/or amount of hydrophilic components, respectively.

An additional advantage of the present invention not found in the prior art relates to the immediate release of beneficial agent if desired. Unlike convention osmotic devices that require an outer layer or film of beneficial agent to accommodate immediate release, an appropriate amount of beneficial agent can be mixed into the latex coating of the present invention. The beneficial agent within the latex coating thus performs multiple functions. That is, an initial dosage of the beneficial agent is released from the latex coating upon exposure with the fluid, e.g., liquid enteral nutritional product. Additionally, and although the beneficial agent need only be dispersible and not necessarily hydrophilic, the beneficial agent acts as a hydrophilic component to form or open passages in the matrix-type membrane for sustained delivery of additional beneficial agent from the core. The use of a beneficial agent as a hydrophilic component also further assists to ensure that passages of adequate size are formed for delivery of beneficial agent therethrough.

EXAMPLE

For purpose of enablement and illustration, and not limitation, the composition of an exemplary dosage form unit is presented. Particularly, the construction of the core of the exemplary dosage form unit is presented below in Table 1 and the construction of the coating is presented in Table 2. All ingredients used in the manufacture of the exemplary dosage form unit are available from suppliers known in the art, such as from Sunstar.

TABLE 1

|  | POSSIBLE RANGE (BY WEIGHT) | PREFERRED (BY WT.) |
|---|---|---|
| FD&C BLUE DYE NUMBER 1 POWDER | 1%–50% | 23.8% |
| HYDROXYPROPYL METHYLCELLULOSE (HPMC) | 5%–30% | 21.8% |
| MAGNESIUM STEARATE | 0.2%–1% | 0.3% |
| DICALCIUM PHOSPHATE (DCP) | 0–25% | 3.6% |
| CELLULOSE ACETATE (CA-398-10) | 25%–50% | 41.7% |
| TRIACETIN | 6%–10% | 8.3% |
| FUMED SILICA (CAB-O-SIL) | 0.25%–0.75% | 0.5% |
| TARGET WEIGHT: 500–510 MG | | |

TABLE 2

|  | POSSIBLE RANGE | PREFERRED |
|---|---|---|
| FMC CA EMULSION (WATER AND 26.6% SOLIDS OF CELLULOSE ACETATE AND SODIUM LAUREL SULFATE) | 25%–50% | 32.00% |
| MALTODEXTRIN (MALTRIN 100) | 5%–35% | 5.45% |
| POLYETHYLENE GLYCOL (PEG 3350) | 5%–35% | 5.45% |
| FD&C BLUE DYE NUMBER 1 POWDER | 0%–35% | 14.70% |
| TRIETHYL CITRATE (TEC) | 30%–50% | 42.40% |
| TARGET WEIGHT: 46–52 MG/TABLET | | 100.00% |

Generally, the exemplary dosage form unit of Tables 1 and 2 is intended for delivery of a blue marker dye into a liquid medical nutritional feeding formula. As such, the beneficial agent for this exemplary embodiment is F.D.&C. Blue Dye No. 1, wherein the core alone has a target content of about 120 mg of the beneficial agent, and the dosage unit as a whole, i.e., including the latex coating, has a target content of about 127 mg. The exemplary dosage form unit of Tables 1 and 2 is fabricated as a tablet approximately 6.5–7.0 mm thick and having square shape of about 10.0 mm to a side.

Tables 3 and 4 below present, for purpose of illustration and not limitation, the acceptance criteria for this exemplary dosage form unit of the present invention. It is understood that alternative criteria can be accomplished by modifying the composition or method of manufacture as needed or desired.

TABLE 3

CORE ACCEPTANCE CRITERIA (IN-PROCESS)

| ATTRIBUTE | METHOD | SPECIFICATION |
|---|---|---|
| HARDNESS |  | >20 SCU |
| FRIABILITY | USP (20 TABLET × 10 MINUTES) | <1.5% |
| THICKNESS | DIMENSIONAL | 0.238"–0.248" |
| TABLET WEIGHT | INDIVIDUAL | 490–518 MG |

TABLE 4

COATED TABLET ACCEPTANCE CRITERIA

| ATTRIBUTE | METHOD | SPECIFICATION |
|---|---|---|
| TOTAL DYE CONTENT | WEIGHT | 125–134 MG |
| DYE RELEASE RATE | IN NORMAL SALINE | MATCH COLOR STANDARD |
| 0–1 MIN |  | > = 1 MG |
| 1–120 MIN |  | > = 10 MG |
| 2–8 HR |  | > = 30 MG |
| 8–22 HR |  | > = 70 MG |
| 22–24 HR |  | > = 1 MG |
| HARDNESS |  | >20 SCU |
| FRIABILITY | USP (20 TABLETS) | <1.5% (NO CHIPS OR CRACK IN COAT) |
| THICKNESS | DIMENSIONAL | 0.258"–0.275" |
| WIDTH | DIMENSIONAL | 0.385"–0.400" |
| TABLET WEIGHT | WEIGHT | 540–565 MG/TABLET |

Method Of Construction

The present invention is further directed to the method of manufacturing the dosage form unit of the present invention. For purpose of illustration and enablement, and not limitation, reference will be made to the method of manufacturing the exemplary dosage form unit set forth in Tables 1–4. It is understood that the materials, quantities and process techniques can be modified within the scope of this invention as necessary or desired to accomplish different desired results or criteria. It further is understood that the following specifications for the method of the invention are provided as guidelines, and not necessarily requirements.

With regard to manufacture of the core of the dosage form unit of the present invention, Table 5 sets forth a tablet formulation for an exemplary batch.

TABLE 5

| INGREDIENT | AMOUNT |
| --- | --- |
| FD&C BLUE DYE #1 POWDER | 24.00KG |
| CA-398-10 NF | 42.00KG |
| TRIACETIN | 8.40KG |
| HPMC | 22.00KG |
| DCP | 3.60KG |
| CAB-O-SIL | 0.50KG |
| MAGNESIUM STEARATE | 0.25KG |
| TOTAL | 100.75KG |

For fabrication of the core, the beneficial agent is mixed with the binding agent. For example, and with regard to the embodiment presented herein, a conventional Sigma mixer is used to mix the CA-398-10NF and FD&C Blue Dye Number 1 for a suitable duration, such as ten (10) minutes. If needed, the plasticizer, e.g., triacetin, is added into the mixture during the initial mixing step, such as by using a dedicated two fluid atomizer for the exemplary embodiment herein. Preferably, this mixture is then allowed to set an appropriate period of time, such as one (1) hour, and is milled, such as by using a Fitzmill device having a #109 screen. The milled mixture can then be added to a conventional ribbon blender to blend therein the hydrophilic agent and tableting aids, such as HPMC and diacalcium phosphate, respectively, as in the present embodiment. Approximately ten (10) minutes is an appropriate period of time for such blending for this embodiment. The standard flow agent, e.g., CAB-O-SIL, is preblended and screened, such as with a #20 screen, before being mixed into the mixture for an appropriate time, such as five (5) minutes. Similarly and the lubricant, e.g., magnesium stearate, is preblended and mixed into the mixture for an appropriate time, such as five (5) minutes. This mixture is then pressed into a preselected core shape, such as a substantially square tablet form as embodied herein.

With regard to manufacture of the coating of the dosage form unit of the present invention, Table 6 sets forth an exemplary batch of coating formulation for the tablets embodied herein. It is noted that the add-on weight of the dried coating for each tablet of this exemplary embodiment preferably is equivalent to about 10.0% of the tablet weight. To account for process losses, however, the amount of coating formulation is increased to the equivalent of about 12.5% of the tablet weight. It also is noted that the only processing solvent used for the fabrication of the coating in this exemplary embodiment is potable water.

TABLE 6

| INGREDIENT | AMOUNT |
| --- | --- |
| FMC CA EMULSION | 155.4GRAMS |
| MALTRIN 100 | 7.0GRAMS |
| FD&C BLUE DYE NUMBER 1 | 19.0GRAMS |
| PEG 3350 | 7.0GRAMS |

TABLE 6-continued

| INGREDIENT | AMOUNT |
| --- | --- |
| TEC | 54.7GRAMS |
| DEIONIZED WATER | 617.1GRAMS |
| TOTAL | 860.2GRAMS |

The coating formulation is manufactured by first mixing approximately one-half (½) the solvent water with the hydrophobic base material and plasticizer if needed. This is accomplished in the present representative embodiment by mixing the plasticizer, e.g., TEC, into the water for a suitable period, such as about two (2) minutes, and then rapidly adding the base material, e.g., the FMC CA emulsion, into the TEC/water mixture. This mixture is stirred under moderate agitation for a suitable time, such as about thirty (30) minutes and processed through a screen, such as a 50/009 screen for consistency.

Separately, the remaining one-half (½) of water is mixed with the hydrophilic components of the coating formulation. For example and as embodied herein, the PEG 3350 is first stirred into the water under moderate agitation for a suitable period, such as about five (5) minutes. The MALTRIN 100 is then added and stirred under moderate agitation for an additional five (5) minutes. This mixture is filtered through an appropriate screen, such as a 50/009 screen for the exemplary embodiment. Any beneficial agents to be contained by the coating also can be added at this time, such as adding the F.D.&C. Blue Dye Number 1 and stirring under moderate agitation for ten (10) minutes or otherwise appropriate period of time.

As a final step of the representative embodiment herein, the two separate mixtures are combined together under moderate agitation for a suitable period, such as about five (5) minutes. The coating formulation is then in condition for application onto the tablet cores. Preferably, agitation of the combined mixture is continued until application of the coating is completed.

It is possible that any of a variety of known procedures can be used for the application of the coating in accordance with the present invention. As embodied herein, for example, it is preferred to apply the coating using a known spraying procedure. Particularly, the preferred embodiment uses a coating apparatus known as a coating pan available from Accelacota, which includes an atomizer to spray the coating formulation onto the cores contained within a rotatable pan. The Accelacota apparatus is operated at an atomizing pressure of about 77–90 psig having an inlet temperature of between about 55 and 65° C., and an outlet temperature of about 43–44° C. The rotatable pan is rotated at about 3 rpm for an initial period, such as about fifteen (15) minutes, and then increased in speed to about 5–7 rpm until coating is completed. Once completed, the rotatable pan is stopped, and the inlet temperature is maintained at a suitable drying temperature, such as about 65° C., for a period of about thirty (30) minutes with the rotatable pan being jogged periodically, such as every five (5) minutes. The tablets are then transferred to suitable drying racks to complete drying under appropriate conditions, such as 55–57° C. for forty-eight (48) hours or more.

The detailed description above is directed the construction and method of making a novel dosage form unit in accordance with the present invention. Particularly, the detailed description discloses a dosage form unit for use in combination with an enteral feeding assembly and method. Further in accordance with an additional aspect of the present invention, the construction and method described in detail above, as appropriately modified, likewise is applicable to dosage form units for parenteral drug delivery systems, as well as to dosage form units for oral delivery. Hence, it will be apparent to those skilled in the art that various modifications and variations can be made in the method and system of the present invention without departing from the spirit or scope of the invention. It therefore is intended that the present invention include modifications and variations that are within the scope of the appended claims and their equivalents.

What is claimed is:

1. A method of forming a dosage unit to deliver a beneficial agent into a fluid, the method comprising the steps of:

forming a core containing at least one beneficial agent dispersible in a fluid and a compatible binding agent to bind the beneficial agent together;

preparing a latex formulation including a mixture containing an emulsion of a substantially hydrophobic base material capable of defining a matrix-type membrane and at least one hydrophilic component dispersible in the fluid; and applying the latex formulation onto the core to form a latex coating thereon, wherein the forming step includes providing cellulose acetate as the binding agent of the core, the forming step further including softening the cellulose acetate with a plasticizer to enhance construction of the core.

2. The method of claim 1, wherein the plasticizer of the softening step is triacetin.

3. The method of claim 1, wherein the preparing step includes mixing an emulsion of cellulose acetate as the base material with the at least one hydrophilic component.

4. The method of claim 1, wherein the applying step includes spraying the latex formulation onto the core.

* * * * *